United States Patent
Colles et al.

(10) Patent No.: US 6,170,947 B1
(45) Date of Patent: Jan. 9, 2001

(54) LIGHT PROTECTION SYSTEM

(75) Inventors: John Colles, Lanarkshire (GB); Joshua Raif, Kiryat Ono (IL)

(73) Assignee: Laser Industries Ltd., Tel Aviv (IL)

( * ) Notice: Under 35 U.S.C. 154(b), the term of this patent shall be extended for 0 days.

(21) Appl. No.: 09/032,392

(22) Filed: Feb. 27, 1998

(30) Foreign Application Priority Data

Feb. 27, 1997 (IT) .................................................... 120348

(51) Int. Cl.$^7$ ...................................................... G02C 7/10
(52) U.S. Cl. .............................................. 351/44; 349/14
(58) Field of Search ............................... 351/44, 45, 158; 349/13, 14, 33, 34, 54, 55; 606/10–12; 219/121.85

(56) References Cited

U.S. PATENT DOCUMENTS

| | | | |
|---|---|---|---|
| 5,020,995 | 6/1991 | Levy | 433/215 |
| 5,180,304 | 1/1993 | Vassiliasdis et al. | 433/224 |
| 5,267,856 | 12/1993 | Wolbarsht et al. | 433/29 |
| 5,280,378 | 1/1994 | Lombardo | 359/199 |
| 5,411,502 | 5/1995 | Zair | 606/10 |
| 5,582,752 | * 12/1996 | Zair | 219/121.85 |
| 5,877,825 | * 3/1999 | Kotler | 349/14 |

FOREIGN PATENT DOCUMENTS

| | | |
|---|---|---|
| 119508 | 10/1996 | (IL) . |
| 120347 | 2/1997 | (IL) . |
| WO 86/03958 | 7/1986 | (WO) . |
| 96/01002 | 4/1996 | (WO) . |

OTHER PUBLICATIONS

"Multiple Pulse Irradiation of Dental Hard Tissue at CO2 Laser Wave Length", D. Fried R.E. Glena et al., SPIE vol. 2394 pp. 41–57. 1995.

"Principles of Optics" Born & Wolf 13.5 pp. 661–664.

"Rational Choice of Lasers Conditions for Inhibition of Caries Progression", J.D. B Featherstone et al., Procc. Of Lasers in Dentistry SPIE vol. 2394pp. 57–67 1995.

"Hard Tissue Ablation with Pulsed CO2 Laser", Thomas Ertl et al., SPIE vol. 1880 pp. 176–181 1993.

"Study of Laser Systems for Dental Hard Tissue Ablation" Vladmir Krapchev 1995.

Seka et al., "Time Dependent Reflection and Surface Temperatures During CO2 Laser Irradiation of Dental Hard Tissues with 100ns Pulses." SPIE vol. 2394/51.

"Einfuhrung—Erfahrungen und Probleme bei der Laseranwendung in der Zahn—Mund—Und Kierferheilkunde", pp. 20–21, 1994.

* cited by examiner

Primary Examiner—Huy Mai
(74) Attorney, Agent, or Firm—Eitan, Pearl, Latzer & Cohen-Zedek

(57) ABSTRACT

A system for protection from light generated by interaction of laser energy with matter is provided. The system, which is designed for use with lasing apparatus having a laser, includes an optical protection device with at least one optical element of a material that transforms between an active state for blocking laser light and an inactive state, where the optical element is transparent. A mechanism for controlling the transformation of the optical element between the inactive and active states, attaches to the optical protection device and the lasing apparatus respectively, and is responsive to the activating and deactivating of the laser, such that when the laser is activated, the control mechanism causes the optical element to transform to the active state and when the laser is deactivated, the control mechanism causes the optical element to transform to the inactive state.

10 Claims, 1 Drawing Sheet

LIGHT PROTECTION SYSTEM

FIELD OF THE INVENTION

Figure 1:
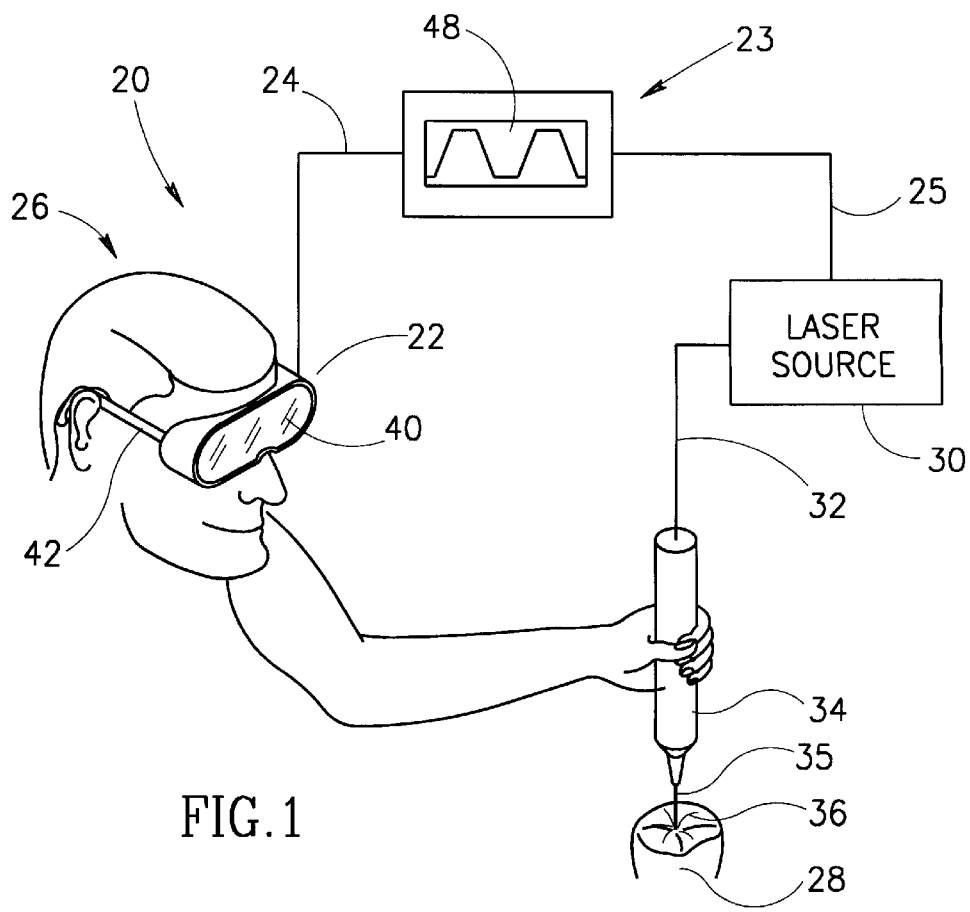

The present invention is directed to a vision protection system from light originated from heat generated when laser radiation interacts with matter. In particular, the present invention is directed to a vision protection system that is active during the period of lasing and inactive during periods of non-lasing in medical applications and in particular in dental applications.

BACKGROUND OF THE INVENTION

A human tooth comprises mainly dentin and enamel tissues, that include the mineral hydroxyapetite. During dental surgery, such as laser drilling or the like, light originated at the interactive area is extremely intense.

As a result of this light, the dentist or other treatment provider, will move their eyes from the operating site during this time of laser activation, in order to avoid real or anticipated retinal burning. Moreover, this movement is a natural, instinctive, reaction to extremely bright, high intensity light.

This creates a problem, for this time period, in which lasing is occurring, is most critical for the success of the dental surgery procedure. During such a period, the dentist's eyes should be focused on the operating site, in order for the dentist to operate with maximum precision.

There are tinted goggles and the like which protect against this intense light. However, the dentist must manually place these goggles on and remove them repeatedly during a single dental surgery. This is both frustrating and inefficient.

SUMMARY OF THE INVENTION

The present invention overcomes the problems of contemporary vision protection devices by providing a vision protection system with eye protection that is activated upon lasing and deactivated once lasing ceases and during non-lasing times. This allows the dentist to wear the eye protection of the system of the invention during the entire procedure, thus avoiding the need to constantly place on and remove the eyewear during lasing and non-lasing periods of the instant dental procedure.

The present invention is preferably designed for use with a lasing apparatus including a laser, and includes an optical protection device with at least one optical element of a material that transforms between an active state for blocking laser light and an inactive state, where the optical element is transparent. A mechanism for controlling the transformation of the optical element between the inactive and active states, attaches to the optical protection device and the lasing apparatus respectively, and is responsive to the activating and deactivating of the laser, such that when the laser is activated, the control mechanism causes the optical element to transform to the active state and when the laser is deactivated, the control mechanism causes the optical element to transform to the inactive state. Such activation's and deactivations of the optical element, corresponding to the activation and deactivation of the laser of the lasing apparatus can continue for as long as desired, and are usually dependent upon the procedure being performed.

BRIEF DESCRIPTIONS OF THE DRAWINGS

The present invention will be described with reference to the accompanying drawings, wherein like reference numerals identify corresponding or like components.

Figure 2:
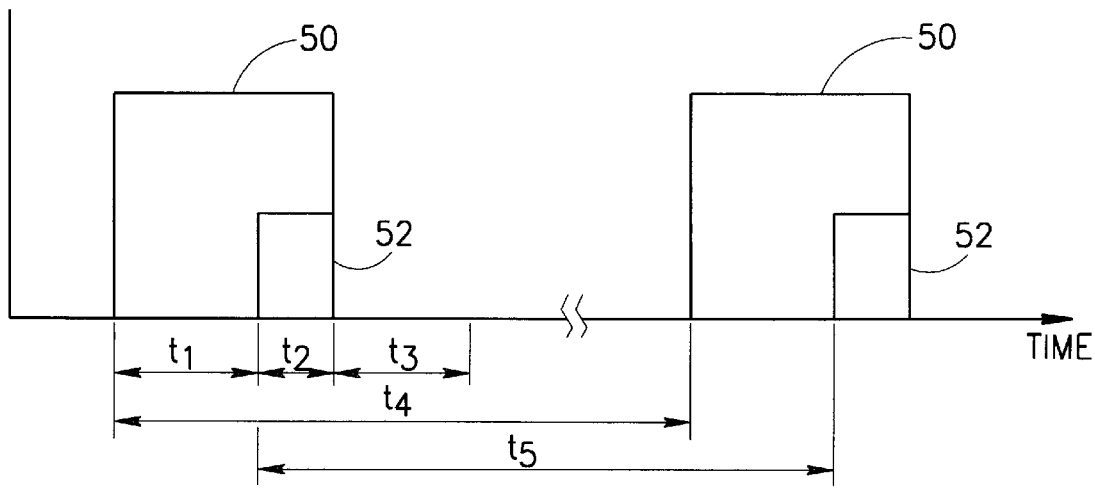

In the drawings:

FIG. 1 is a diagram of the present invention in use in a dental surgical procedure; and FIG. 2 is a timing diagram for the optical protection device with respect to the pulses of the lasing apparatus.

DETAILED DESCRIPTION OF THE DRAWINGS

FIG. 1 shows a system 20 in accordance with the present invention, used during the performance of dental surgery. The system 20 includes a lasing apparatus, an optical protection device 22, both in electrical communication with a controller 23, by lines 24, 25. The system 20 is preferably used by a dentist 26 in performing a procedure, such as drilling, root canal, or the like on a tooth 28.

The lasing apparatus preferably includes a laser source 30 connected preferably by an articulated arm 32 or the like to a hand piece 34. The radiation conveying handpiece 34 allows the dentist 26 or technician to control the emitted laser radiation 35, for operating on a tooth 28, or other tissue. Some of the radiation 36 generated by the heat resulting from the interaction between the laser radiation 35 and the tooth 28, is in the visible spectrum.

The preferred laser source 30 is a 9.6 $\mu$m $CO_2$ laser, as described in Israel Patent Application No. 120347 filed Feb. 27, 1997, assigned to the assignee of the present invention, the entire patent application incorporated by reference herein. This laser may be used with the $CO_2$ systems for vaporizing any one of hard tissue and deposits on hard tissue disclosed in U.S. patent application Ser. No. 08/711,164 filed Sep. 5, 1996, with the system disclosed in Israel Patent Application No. 119508 filed Oct. 28, 1996, both assigned to the assignee of the present invention, both of these applications in their entireties, incorporated by reference herein, and with the system described in PCT Patent Application GB96/01002, filed Apr. 26, 1996 assigned to Medical Laser Technologies of Scotland, the disclosure of which is also incorporated by reference herein.

The laser radiation 35 could be directed to the tooth 28 in accordance with any of the methods described in Israel Patent Application No. 120347, in U.S. patent application Ser. No. 08/711,164, in Israel Patent Application No. 119508 and in MLT's PCT application (listed above). For example, in conventional dental procedures, such as drilling, the laser radiation is delivered in pulses of approximately 60 microseconds (t2 in FIG. 2) with each pulse separated by approximately 7 milliseconds (t5 in FIG. 2), at approximately 50 millijoules, in the 9.6 micrometer band. It may also be directed using a scanner, such as the one described in coassigned U.S. Pat. Nos. 5,411,502 and 5,582,752, the entire content of which is incorporated herein by reference.

The optical protection device 22, preferably are goggles with a optical element 40 and a optical element support 42 adapted for the shape of the head so as to completely envelop the eyes of the dentist 26. While a single optical element 40 is shown, alternate embodiments may include multiple optical elements, such as two, one for each eye, with a corresponding optical element support. The optical element(s) is preferably of liquid crystal polymer, capable of being activated to an active state, so as to block the light radiation 36, in response to an electrical signal received through the line 24 from the controller 23. Commercially available examples of these goggles are CrystalEyes® 2 Stereo Eyewear, from StereoGraphics Corporation 2171 East Francisco Blvd., San Rafael, Calif. 94901 and VR Surfer, from VRex, Inc., 8 Skyline Drive, Hawthorne, N.Y. 10532, both of these goggles being modified so as to receive electrical signals for activating and deactivating the optical element(s)

The controller 23 includes electronics connected to preferably a master oscillator 48 that sends an electrical pulse through the line 24 to the optical element 40, in order to activate the liquid crystal material, such that the optical element 40 becomes radiation (light) blocking at times when the lasing apparatus is pulsing (emitting radiation).

Turning also to FIG. 2, the electronics and master oscillator 48 of the controller 23 are such that the timing of the optical element, indicated by line 50, is coordinated with the timing of the individual laser pulses, indicated by line 52. Initially, the lasing apparatus is not lasing (emitting laser radiation for time t2 in controlled pulses, as detailed above) thus, the optical element 40 is initially in an inactive state (its preferred default state), where it is transparent to light. Upon sensing an activation of the lasing apparatus (as the dentist 26 activates the handpiece or footswitch causing laser firing), the electronics sense this activation and activate the master oscillator, that pulses, these pulses initiating optical element 40 activation approximately 1 millisecond (t1), before the firing of the lasing apparatus. This approximately 1 millisecond lag time (t1), is the approximate time for the optical element 40 to transform from the inactive state, to an active state, where the optical element 40 is of sufficient opacity to block the laser radiation (light). These electronics are such that they continue to sense the laser pulse (emitting laser radiation) (t2), and upon termination of the pulse, will signal the oscillator 48 to cease electronic pulsing of the optical element 40, such that the optical element 40 returns to the inactive state. Should the laser remain activated by the dentist 26, the optical element 40 will again be transformed from the inactive to the active state back to the inactive state, in correspondence with the laser pulse, in accordance with the procedure described above. This operation may continue for as long as desired for the dentist to complete the requisite procedure. Preferably, each successive optical element activation/deactivation, and successive laser pulse are approximately 7 milliseconds apart (t4, t5).

While embodiments of the present invention have been described so as to enable one skilled in the art to practice the present invention, the preceding description is intended to be exemplary and should not be used to limit the scope of the invention, which should be determined by reference to the following claims.

What is claimed is:

1. A system for protection from light generated by interaction of laser energy with matter comprising:

a lasing apparatus including a laser for emitting radiation;

optical protection means including at least one optical element of a material that transforms between inactive and active states; and means for controlling the transformation of the at least one optical element between the inactive and active states, the controlling means including means responsive to the activation of said laser, such that when the laser is activated, the at least one optical element transforms from the inactive state to the active state and when the laser is not activated, the at least one optical element transforms back to the inactive state.

2. The system of claim 1, wherein the material that transforms between the active and inactive states includes a liquid crystal polymer.

3. The system of claim 1 wherein the laser is a $CO_2$ laser and the matter said laser interacting with is dentin or enamel.

4. The system of claim 3 wherein the laser is operative in the 9.6 $\mu$m band.

5. The system of claim 1 wherein said lasing apparatus includes a scanner.

6. A system for protecting the vision of an operator against light generated from interaction of a laser with a matter comprising:

optical protection means including at least one optical element of a material that transforms between an active and an inactive state; and means for controlling the transformation of the at least one optical element between the inactive and active states, the controlling means including means responsive to the activation of said laser, such that when the laser is activated, the at least one optical element transforms from the inactive state to the active state and when the laser is not activated, the at least one optical element transforms back to the inactive state.

7. The system of claim 6, wherein the material that transforms between the active and inactive states includes a liquid crystal polymer.

8. The system of claim 6 wherein the laser is a $CO_2$ laser and the matter said laser interacting with is dentin or enamel.

9. The system of claim 6 wherein the laser is operative in the 9.6 $\mu$m band.

10. The system of claim 6 wherein said lasing apparatus includes a scanner.

* * * * *